United States Patent
Thomsen et al.

(10) Patent No.: US 9,551,647 B2
(45) Date of Patent: Jan. 24, 2017

(54) PULSED UV-LIGHT SOURCE

(71) Applicant: NKT PHOTONICS A/S, Birkerød (DK)

(72) Inventors: Carsten L. Thomsen, Virum (DK); Frederik Donbaek Nielsen, København V (DK); Sascha Hauser, Rechtenbach (DE); Eberhard Riedle, München (DE); Maximilian Bradler, München (DE)

(73) Assignee: NKT PHOTONICS, Birkerod (DK)

( * ) Notice: Subject to any disclaimer, the term of this patent is extended or adjusted under 35 U.S.C. 154(b) by 600 days.

(21) Appl. No.: 13/648,697

(22) Filed: Oct. 10, 2012

(65) Prior Publication Data

US 2014/0091240 A1   Apr. 3, 2014

(30) Foreign Application Priority Data

Oct. 1, 2012   (DK) .................................. 2012 70597

(51) Int. Cl.
  *G02F 1/35*   (2006.01)
  *G01N 21/00*   (2006.01)
  (Continued)

(52) U.S. Cl.
  CPC ............ *G01N 21/00* (2013.01); *G01N 21/255* (2013.01); *G02F 1/3501* (2013.01); *G02F 2001/3528* (2013.01); *H01S 3/09* (2013.01)

(58) Field of Classification Search
  None
  See application file for complete search history.

(56) References Cited

U.S. PATENT DOCUMENTS 5,038,352 A  *  8/1991  Lenth .................. H01S 5/141
                                            359/326
5,179,562 A     1/1993  Marason et al.
                        (Continued)

FOREIGN PATENT DOCUMENTS

WO   WO 2009/095022 A2   8/2009
WO   WO 2012/028152 A1   3/2012
WO       2012/069612 A1   5/2012

OTHER PUBLICATIONS

Search Report and Opinion issue on Mar. 1, 2013, by the Danish Patent and Trademark Office in corresponding Danish Patent Application No. PA 2012 70597. (5 pages).

(Continued)

*Primary Examiner* — Hemang Sanghavi
(74) *Attorney, Agent, or Firm* — Buchanan Ingersoll & Rooney PC

(57) ABSTRACT

The disclosure relates to a tunable optical light source spanning the UV-range and possible also the visible and near-IR wavelengths. The tunable optical light source includes an input light source, a focusing element, a non-linear crystal arranged to convert the frequency of at least part of the output spectrum of the super continuum source, and a holding unit for the non-linear crystal. The input light source is a super continuum light source with a spectral bandwidth of at least about 300 nm and the holding unit is adjustable for changing the frequency converted output wavelength of the non-linear crystal $w_{fc}$ such that the lowest obtainable output wavelength $w_{UV}$ of said tunable light source is ultraviolet. The disclosure further relates to an illumination source and an optical measurement system.

44 Claims, 16 Drawing Sheets

(51) Int. Cl.
*G01N 21/25* (2006.01)
*H01S 3/09* (2006.01)

(56) References Cited

U.S. PATENT DOCUMENTS

| | | |
|---|---|---|
| 7,202,993 B2* | 4/2007 | Tauser et al. .................. 359/326 |
| 2009/0097512 A1* | 4/2009 | Clowes et al. .................. 372/21 |
| 2010/0085631 A1* | 4/2010 | Kusukame ............ G02F 1/3525 |
| | | 359/328 |
| 2011/0063718 A1* | 3/2011 | Tu et al. ....................... 359/327 |
| 2011/0069375 A1* | 3/2011 | Lin et al. ...................... 359/328 |
| 2012/0049092 A1* | 3/2012 | Tu ............................ G02F 1/353 |
| | | 250/504 R |
| 2012/0099340 A1 | 4/2012 | Buchter |
| 2012/0236314 A1 | 9/2012 | Fermann et al. |

OTHER PUBLICATIONS

G. Szabo et al., "Broadband Frequency Doubler for Femtosecond Pulses", Applied Physics B., vol. 50, pp. 51-54, 1990.

Peter Baum et al., "Tunable Sub-10-FS Ultraviolet Pulses Generated by Achromatic Frequency Doubling", Optics Letters, vol. 29, No. 14, Jul. 15, 2004, pp. 1686-1688.

E. Riedle et al., "Generation of 10 to 50 FS Pulses Through All of the Visible and the NIR", Applied Physics B, pp. 457-465, 2000.

Fabio Baronio et al., "Second and Third Order Susceptibilities Mixing for Supercontinuum Generation and Shaping", Optical Fiber Technology, vol. 18, 2012, pp. 283-289.

* cited by examiner

Fig. 2: Prior art from Szabo

Fig. 5: Prior art

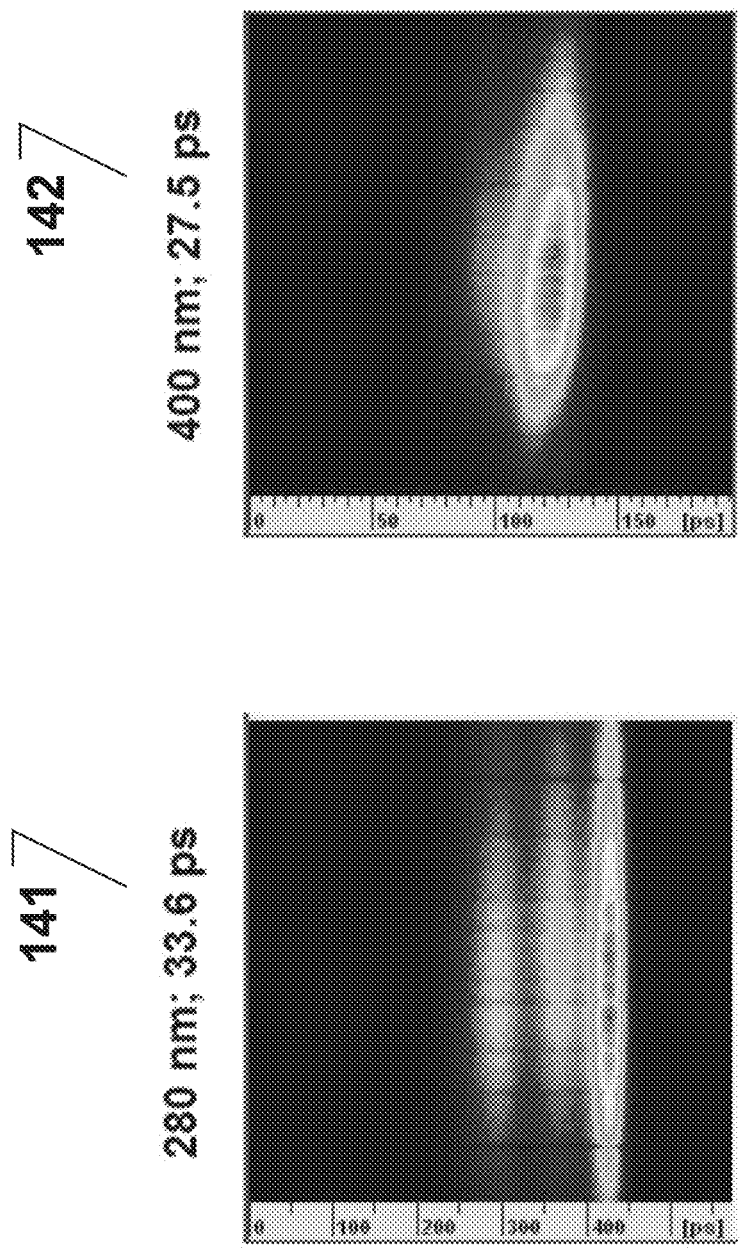

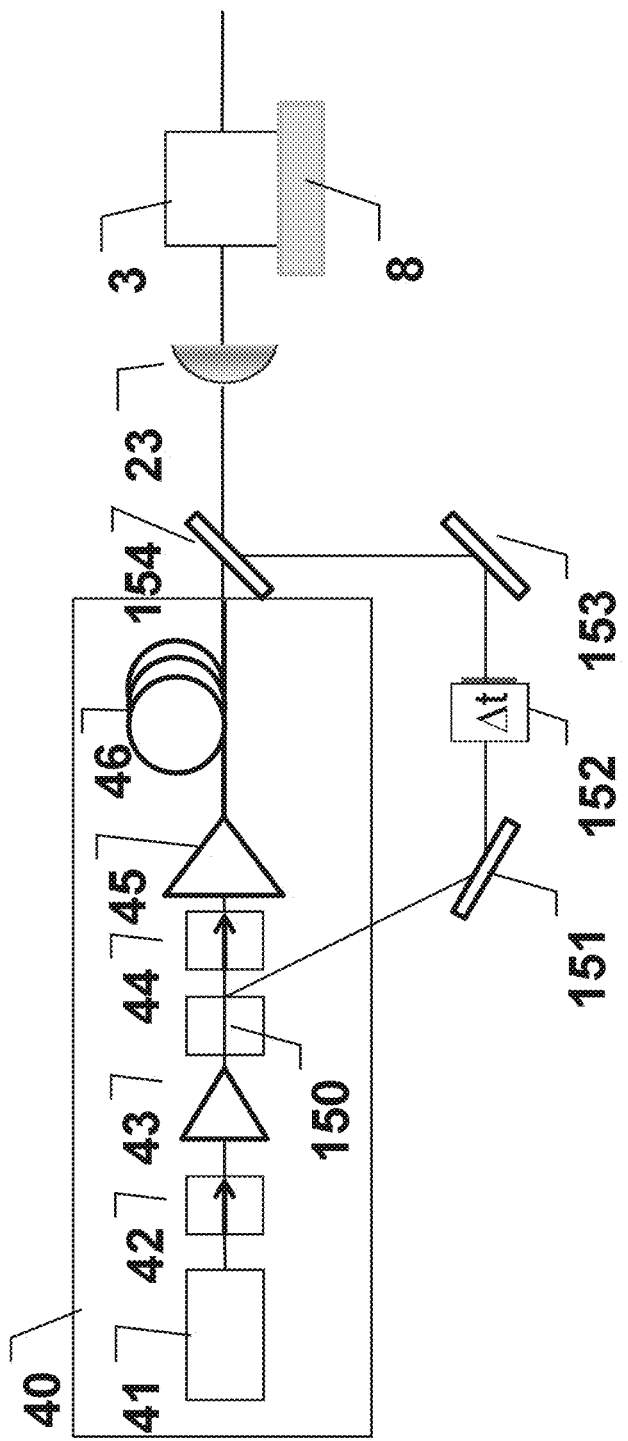
Fig. 15: SFM crystal

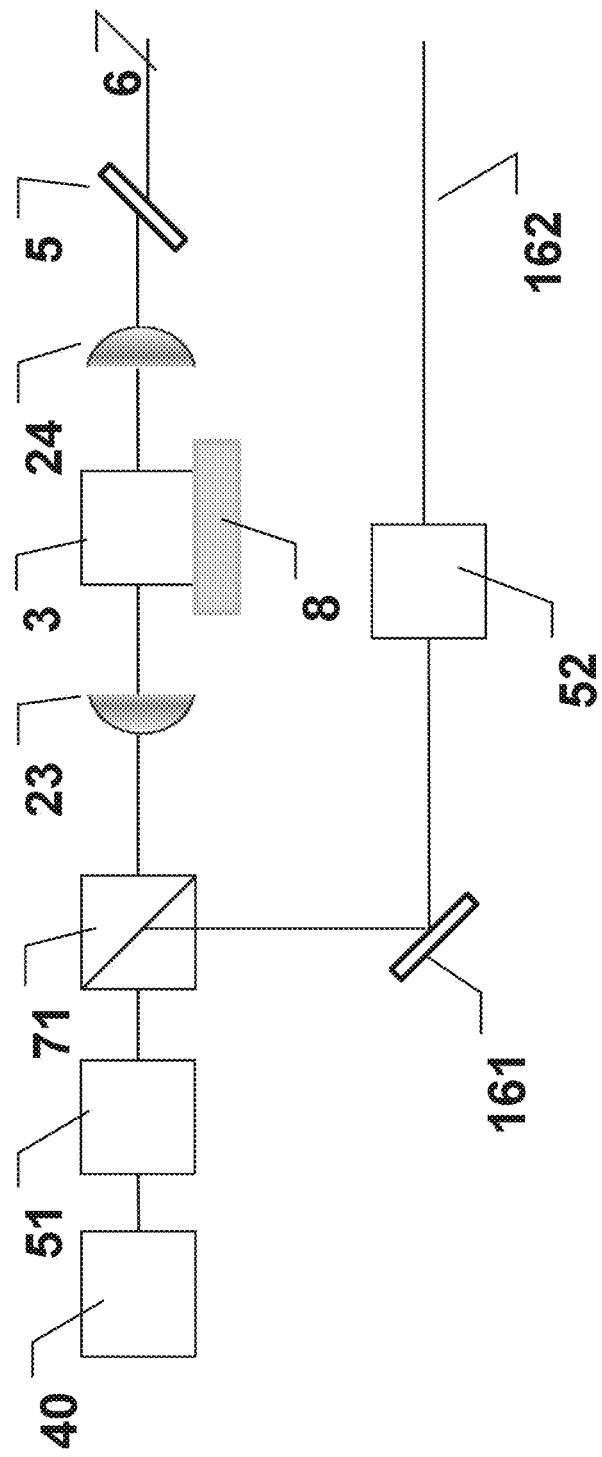
Fig. 16: Broadly tunable source

PULSED UV-LIGHT SOURCE

TECHNICAL FIELD

The present invention relates to a tunable pulsed light source spanning the UV range and suitable for use in an illumination source and/or an optical measurement system. The invention also relates to an illumination source as well as an optical measurement system comprising such tunable pulsed light source.

BACKGROUND ART

Optical measurement systems are frequently used to analyze biological and chemical substances. In e.g. confocal microscopes a fluorophor is added to the substance under test. A laser light is used to excite the fluorophor, and when it subsequently decays radiatively a camera can detect its position.

Light is also used to study physical, chemical and biological reactions, which typically occur on a femtosecond (fs) to nanosecond (ns) scale. This is conventionally done by having a pump laser and a fs probe laser, which is slightly delayed compared to the pump laser.

In order to analyze many different samples and substances the optical measurement system should preferably contain several laser wavelengths. This can be achieved by combining multiple single line width lasers and/or having a tunable light source.

Applications within the field span light sources all the way from the UV (10-400 nm) through the visible (400-800 nm) to the near-IR region (800-2500 nm). E.g. to analyze spectra of gaseous benzene it is often preferred to measure spectra from 210 nm to 300 nm, whereas e.g. to analyse wheat it is normally preferred to span from 750 nm to 2500 nm.

The preferred choice of light source varies for different applications. Some examples are thermal sources or Ti:sapphire lasers for near-IR wavelengths, and Ti:sapphire based non-collinearly phase matched optical parametric oscillators for visible and UV wavelengths. Within the last decade fiber-based systems have also been used to generate broadband sources, examples include frequency combs spanning 530 nm to 2100 nm (e.g. FC1500-250-WG Optical Frequency Synthesizer from Menlo Systems) and super continuum (SC) sources spanning 400 nm to 2400 nm (e.g. SuperK EXR-15 from NKT Photonics A/S or WhiteLase SC400 from Fianium Ltd). Other examples include sub-nanosecond pulsed LEDs, such as e.g. the PLS series from PicoQuant, which have pulselengths down to 500 ps and can reach up to 80 µW output power in the visible range and around 1 µW in the UV. Here PicoQuant notes that 1 µW is still sufficient to use the source as an efficient fluorescence excitation source.

Another approach is to frequency double, triple or quadruple optical pulses to obtain shorter wavelengths. These processes are commonly referred to as second, third and fourth harmonic generation. For brevity, all these processes will in the following be described as frequency doubling, i.e. the term frequency doubling should be understood to include harmonic generation of any order.

Frequency doubling can be obtained by sending light pulses with a high intensity through a non-linear crystal. Inside the non-linear crystal some of the light photons combine to create light at the doubled frequency (and thus half the wavelength) whereas other parts of the light traverse the crystal without being doubled; see FIG. 1. Accordingly the output beam from the crystal will contain light at both the original frequency f1 and the doubled frequency 2f1. The amount of light at the different frequencies depends on the degree of phase matching between the photons at the fundamental and doubled frequency (i.e. f1 and 2f1). The phase matching again depends on the intensity, spectral content and angular dispersion of the incoming light, but also on the crystals material, length and how it is cut.

For un-dispersed incoming light, the path length inside the crystal where there is phase matching is inversely proportional to the bandwidth of the incoming light. Thus extremely short crystals have been used for frequency doubling broad band pulses, for example Szabo states that for frequency doubling a 50 fs beam at 496 nm the crystal length should be shorter than 0.07 mm if the light is un-dispersed (*Broadband frequency doubler for femtosecond pulse*, G. Szabo and Z Bor, *Appl. Phys. B*. 50, page 51-54, 1990, see first paragraph on page 51).

Frequency doubling in short non-linear crystals is enabled by increasing the light intensity, since the degree of frequency doubling generally increases with the intensity of the incoming light. However, high intensity light will often lead to degradation of the crystal and hence limit its lifetime. This is in particular the case for conversion to wavelengths in the UV region.

For broad band sources, it has been shown that angularly dispersing the light before the non-linear crystal enables obtaining phase matching over a wider bandwidth. E.g. the prior mentioned reference by Szabo showed that dispersing the beam on a grating prior to the non-linear crystal enables doubling 10 fs pulses at 496 nm in a 1 mm long crystal, see FIG. 2. For reference 10 fs pulses at 496 nm must have a bandwidth of at least 25 nm (Fourier transform limit).

The idea of dispersing the light before the crystal was experimentally demonstrated in a paper by Baum (*Tunable sub-10-fs ultraviolet pulses generated by achromatic frequency doubling*, Peter Baum, Stefan Lochbrunner, Eberhard Rielde, *Optics Letters*, vol. 29, no. 14, Jul. 15, 2004, page 1686-1688). Here a set of prisms between the laser and the doubling crystal are used to enhance the doubling bandwidth by a factor of 80 and obtain a tunable source from 275-375 nm with <10 fs pulse length and a 360 µm thick BBO crystal, see FIG. 3.

A similar approach has furthermore been used to demonstrate a tunable source from 460 nm to 900 nm with <50 fs pulse length (*Generation of 10 to 50 fs pulses through all of the visible and the NIR, Appl. Phys. B*, 457-465, 2000, E Riedle, M. Beutter, S. Lochbrunner, J. Piel, S. Schenkl, S. Spörlein, W. Zinth).

Such a system is well suited for experiments requiring tunable very short fs pulses in the UV or visible range. However, it has a large cost, is complex to operate and requires highly skilled operators, and thus also has a large cost of ownership.

A lot of bio-optical applications require time resolved measurements but not necessarily on a short fs scale. Some examples include time resolved fluorescence, time correlation single photon counting, single molecule detection, intrinsic fluorescence, time resolved photoluminescence, UV polymerisation of resin, DNA sequencing, confocal microscope, FLIM, FRET, flow cytometry, cell-sorting, spectroscopy and food analysis.

Thus there is a commercial market for a low cost tunable light source spanning the UV-range with an output of at least 1 µW. The addressable market further increases if the tunability can be extended into the visible and/or near-IR wavelengths.

DISCLOSURE OF INVENTION

In view of the foregoing an object of the present invention is to provide a low cost tunable light source spanning the UV-range and possible also the visible and near-IR wavelengths.

This and other objects have been solved by the invention as defined in the claims and as described herein below.

It has been found that the invention and embodiments thereof have a number of additional advantages which will be clear to the skilled person from the following description.

The tunable pulsed light source of the invention comprises a super continuum light source with a pulse length of at least about 300 femtosecond and a non-linear crystal, which can be adjusted to enable tuning the output spectrum of the tunable source such that it comprises wavelengths in the UV range and simultaneously having an output of at least about 1 µW. The UV range is herein defined to be in the range from about 10 to about 400 nm.

In view of the prior art the traditional approaches for frequency doubling of broad band light sources are to use very short non-linear crystals and increase the intensity and peak power of the light incoming on said non-linear crystal and/or to disperse the light prior to reaching said non-linear crystal.

Fiber laser super continuum sources (super continuum sources where the amplifier chain is all-fiber) are very broad band, and compared to the cited prior art have low peak power. Hence heretofore the present invention it was expected that it would be very difficult to frequency double these light sources and accordingly that a useful output using such super continuum light source would be practically impossible to achieve.

Surprisingly, the inventors have discovered that it is possible to frequency double SC sources with a relatively simple and inexpensive frequency doubling set-up, and that the output spectral density can be in the order of µW, such as at least 1 µW, which is sufficient to detect the pulses and hence enabling use of such light source for a number of bio-optical measurements.

The tunable pulsed light source of the invention comprises
- an input light source;
- a focusing element;
- a non-linear crystal arranged to convert the frequency of at least part of the output spectrum of said super continuum source; and
- a holding unit for said non-linear crystal, wherein the input light source is a super continuum light source.

The super continuum light source (in the following also referred to as a SC light source) has a spectral bandwidth of at least about 100 nm. The holding unit is adjustable such that it is suitable for changing the frequency converted output wavelength of the non-linear crystal $w_{fc}$ to provide that the lowest obtainable output wavelength $w_{UV}$ of the tunable light source is in the UV range.

Furthermore $w_{fc}$ is defined as the central output wavelength of the frequency converted beam after the non-linear crystal at the given position, orientation and temperature of the crystal.

The lowest obtainable output wavelength $w_{UV}$ of the tunable light source is defined as the lowest wavelength where it is possible to achieve an output power of at least about 1 µW.

In an embodiment the holding unit is adjustable for changing the frequency converted output wavelength of the non-linear crystal to provide that a least one output wavelength in the ultraviolet range has a power of at least about 1 µW, such as at least about 2 µW, such as at least about 5 µW, such as at least about 10 µW, such as at least about 20 µW, such as at least about 50 µW.

Advantageously the non-linear crystal is arranged to convert the frequency of the SC source. This includes both non-linear crystals optimized for frequency doubling, sum frequency mixing and other non-linear conversions.

In one embodiment the lowest obtained output wavelength $w_{UV}$ is less than 380 nm, such as less than 360 nm, such as less than 320 nm, such as less than 300 nm, such as less than 280 nm, such as less than 260 nm.

As mentioned in the background section, the central output wavelength of the frequency doubled beam $w_{fc}$ is determined by the phase matching condition. Thus it depends on how the light enters, traverses and exits from the non-linear crystal and on the temperature of the crystal. Thus in one embodiment the adjustment of the non-linear crystal is performed by changing its position, orientation and/or temperature.

Surprisingly it was found that nearly any translation or rotation stage can be used for the non-linear crystal. Examples comprise Newport or Thorlabs standard mirror mounts, rotation stages and translation stages.

The efficiency of the frequency doubling inside the non-linear crystal depends on the beam size. Hence, in one embodiment the holder unit is adjustable to position the non-linear crystal in the focus position of the light from the focus element.

In one embodiment the adjustment of the holder is computer controlled, so that the light source has a computer controlled output wavelength. In this embodiment the holder is advantageously in digital connection (with wire or wireless) with a computer which is programmed to adjust the holder to the desired position(s). Thereby the output wavelength $w_{fc}$ can be controlled by the computer. The computer e.g. received feed back from the output light.

In one embodiment the holder unit is arranged to change the phase-matching angle and thereby the output wavelength $w_{fc}$ without changing the distance to the focusing element.

However, it is known from literature that some non-linear crystals degrade with time due to the high intensity light impinging on them, see e.g. U.S. Pat. No. 5,179,562. This degradation is typically very local and limited to the area where high intensity light impinges on the crystal. In one embodiment of the invention the holder of the non-linear crystal enables both adjusting the non-linear crystal to enable tuning the light source and moving the non-linear crystal with respect to the incoming beam so that it impinges on a new spot on the crystal, when the degradation of the currently used spot reaches a threshold value. An example for detecting the threshold value and moving the non-linear crystal is shown in patent application WO 2009/095022.

As prior noticed, SC sources have limited peak power. Typically the output from SC sources is either diverging or collimated with a spot size on the order of mm. In order to achieve high intensity on the non-linear crystal it has been found to be advantageous to include a focusing element before the non-linear crystal. Examples of such focusing elements comprise mirrors and/or lenses, and in one embodiment the focusing element is an achromat. In one embodiment the focusing element comprises several mirrors and/or lenses. As will be clear to one skilled in the art, the focusing element can either be integrated in the SC source or it can be an external part relative to the SC source. Thus in one embodiment the focusing element is placed inside the SC source and in one embodiment the focusing element is placed outside the SC source.

If the non-linear crystal is placed in the focal point from the focusing element, then the beam size at the crystal is inversely proportional to the numerical aperture of the focusing element. Thus to achieve frequency doubling a minimum numerical aperture is required.

Advantageously the output from the focusing element has a numerical aperture of from about 0.001 to about 0.25.

In one embodiment the output from the focusing element has a numerical aperture of above 0.001, such as above 0.005, such as above 0.01, such as above 0.015, such as above 0.02.

In one embodiment the output beam from the focusing element has a numerical aperture which is below 0.25, such as below 0.2, such as below 0.15, such as below 0.1, such as below 0.08, such as below 0.06.

Furthermore it has been found that the optimal numerical aperture depends on the wavelength. Hence in one embodiment the light source comprises an adjustable NA of the output beam from the focusing element, such as an optical telescope positioned before the focusing element or a variable path length device.

In one embodiment the focal length of the focusing element is such as at least 9 mm, such as greater than 14 mm, such as greater than 19 mm, such as greater than 24 mm, such as greater than 29 mm.

For conversion to the ultraviolet it has found to be important using a non-linear crystal. Advantageously the non-linear crystal is suited for the converted wavelengths. Examples of suitable crystals are lithium triborate ($LiB_3O_5$=LBO), cesium lithium borate ($CsLiB_6O_{10}$=CLBO), β-barium borate (β-$BaB_2O_4$=BBO), bismuth triborate ($BiB_3O_6$=BIBO), cesium borate ($CsB_3O_5$=CBO), Yttrium calcium oxyborate (YCOB), strontium beryllium borate ($Sr_2Be_2B_2O_7$=SBBO) and potassium aluminum borate ($K_2Al_2B_2O_7$=KAB).

In one embodiment the non-linear crystal is Type I cut, meaning that two photons having ordinary polarization with respect to the crystal will combine to form one photon with double the frequency and extraordinary polarization. It is noted that the maximal numerical aperture (NA) of the non-linear crystal depends on the crystal material, e.g. a BIBO crystal can obtain a larger NA than a BBO-crystal.

The crystal has a length defined as the length that the optical beam traverses inside said crystal when it is used for frequency doubling. Some companies as e.g. Eksma Optics denote this as the crystal thickness.

In one embodiment the length of the crystal is at least 0.5 mm, such as larger than or equal to 1 mm, larger than or equal to 1.5 mm, larger than or equal to 2 mm, larger than or equal 3 mm, larger than or equal to 4 mm, such as larger than or equal to 5 mm, such as larger than or equal to 6 mm, such as larger than or equal to 7 mm.

The focusing element provides a focal point and the light will from the focusing element traverse a focal length to the focal point.

Due to the focusing element, the light will diverge after having traversed its focal length. In one embodiment the focal point is inside or close to the non-linear crystal. The frequency doubled light after the non-linear crystal will in general be weak. In one embodiment the light source further comprises a collimating element receiving the beam from the non-linear crystal. Here collimating is defined in wide terms as an element that decreases the width of the beam e.g. over a typical working range used in a lab in order to enable measuring it. In one embodiment the collimating element is or comprises a lens or mirror. In one embodiment the collimating element is a lens made of a material with high UV transmission.

Furthermore it might be advantageous including a wavelength filter after the non-linear crystal to remove light at unwanted wavelengths, e.g. the light which is not frequency doubled inside the non-linear crystal. Accordingly, in one embodiment the light source comprises a wavelength filter such as a bandpass filter or low pass filter, e.g. a filter that has high transmission for UV light and very low transmission for visible light. In one embodiment the wavelength filter is an optical glass filter, a low pass filter, a pass band filter and/or a dicroic mirror.

The simple frequency conversion scheme according to the invention has found to be able to frequency double light from substantially any SC source. However, the spectral output and tunability will depend on the specific architecture of SC source. Furthermore the thermal load on the non-linear crystal and the amount of light outside the UV range will depend on whether the SC source is filtered prior to entering the non-linear crystal. Accordingly, some preferred embodiments of the SC source will be described in the following.

In one embodiment the super continuum (SC) source comprises a pulsed master oscillator, one or more amplifiers and a non-linear fiber which transforms the input pulses into a broad band super continuum. In the following the repetition rate, pulse length and peak power after the SEED will be denoted $f_{SEED}$, $t_{SEED}$ and $P_{SEED}$. The corresponding properties after the last amplifier will be denoted $f_{MOPA}$, $t_{MOPA}$ and $P_{MOPA}$. FIG. 4 shows an example of such a SC source with two sets of amplifiers, each separated by an isolator.

As will be clear to the skilled person a similar SC source could be built using either fewer or more amplifiers and isolators. SC sources can also be based on a Q-switch SEED laser, as e.g. the SuperK Compact from NKT Photonics A/S. Inside the non-linear fiber the super continuum spreads in time due to the chromatic dispersion of the non-linear fiber. As the chromatic dispersion is wavelength dependent, different wavelength of light will in general be offset with respect to each other and will leave the non-linear fiber at a different time. Furthermore the pulse duration will vary as a function of the wavelength. As prior described the pulse length of the super continuum source $t_{SC}$ is defined as the shortest pulse length of the SC source when measured over the visible range (400-800 nm). Furthermore $t_{SC}$ will increase with the length of the non-linear fiber. This will decrease the intensity of the light impingent on the non-linear crystal and hence the efficiency of the frequency doubling. Accordingly, in one embodiment of the light source of the invention, the length of the non-linear fiber is less than 10 m, such as less than 5 m, such as less than 2 m, such as less than 1 m, such as less than 0.5 m.

In one embodiment the non-linear fiber is tapered along at least a length section along its longitudinal axis.

In one embodiment the SEED laser wavelength is between 1000 and 1100 nm.

In one embodiment of the invention the pulse length of the SC source $t_{sc}$ is at least 500 fs, such as more than 1 ps, such as more than 2 ps, such as more than 5 ps, such as more than 8 ps, such as more than 10 ps, such as more than 15 ps, such as more than 25 ps.

In one embodiment of the invention the pulse length of the SC source $t_{sc}$ is less than 100 ps, such as less than 50 ps, such as less than 25 ps, such as less than 15 ps, such as less than 10 ps, such as less than 8 ps, such as less than 5 ps, such as less than 2 ps, such as less than 1 ps.

Here $t_{SC}$ is defined as the shortest pulse length of the SC source when measured over the visible range (400-800 nm) with a resolution of 1 nm. This pulse length can e.g. be measured on a streak camera.

In one embodiment of the invention the SC source furthermore comprises a pulse picker, which is placed between the SEED and the last amplifier before the non-linear fiber and is arranged to enable reducing the repetition rate to $f_{MOPA}$ which is lower than or equal to $f_{SEED}$.

In one embodiment of the invention the repetition rate before the non-linear fiber $f_{MOPA}$ is at least 500 kHz, such as more than 1 MHz, such as more than 5 MHz, such as more than 10 MHz, such as more than 40 MHz, such as more than 60 MHz.

In one embodiment of the invention the pulse length before the non-linear fiber $t_{MOPA}$ is at least 300 fs, such as more than 500 fs, such as more than 1 ps, such as more than 2 ps, such as more than 5 ps, such as more than 8 ps, such as more than 10 ps, such as more than 15 ps, such as more than 25 ps, such as more than 50 ps, such as more than 100 ps.

In one embodiment of the invention the pulse length before the non-linear fiber $t_{MOPA}$ is less than 1 ns, such as less than 500 ps, such as less than 100 ps, such as less than 50 ps, such as less than 25 ps, such as less than 15 ps, such as less than 10 ps, such as less than 8 ps, such as less than 5 ps, such as less than 2 ps, such as less than 1 ps.

In one embodiment of the invention the non-linear fiber is a micro-structured silica fiber such as e.g. the "SC-5.0-1040" or the "SC-5.0-1040-PM" fiber from NKT Photonics A/S, Denmark.

In one embodiment of the invention the non-linear fiber is tapered along its longitudinal axis to increase the amount of light below 450 nm and/or reduce the noise of the super-continuum source and/or reduce the length of the non-linear fiber. An example of such a taper can be found in patent application WO2012028152.

In one embodiment the non-linear fiber is followed by a wavelength filter prior to entering the non-linear crystal. The wavelength filter removes the wavelength part of the super-continuum spectrum, which does not contribute to frequency double light into the UV, but gives a thermal load on the non-linear crystal. In one embodiment the filter is an optical glass filter, a low pass filter, a pass band filter, a dicroic mirror, a low pass or a bandpass filter.

Furthermore frequency doubling only works for one polarization of light, whereas the other transverses the non-linear crystal nearly unaffected and furthermore may add undesired thermal load to it. In one embodiment of the invention there is a polarizing element between the SC source and the non-linear crystal. The polarizing element e.g be Glan-Taylor polarizing prisms (e.g. a Glan-Taylor alpha-BBO prism from Laser components), broad band polarization splitter cubes, polarizers or wire grids.

In one embodiment the output of the SC source is polarized. Here polarized is taken to mean that the polarization extinction ratio of the visible part of the super continuum is more than 10 dB. A polarized SC source can e.g. be obtained by using a polarization maintaining or polarizing non-linear fiber inside the SC source.

In general, the tunability of the light source increases with the width of the spectral region impinging on the crystal. Accordingly in one embodiment the spectral width of the light impinging on the non-linear crystal is broader than 100 nm, such as broader than 200 nm, such as broader than 300 nm, such as broader than 400 nm, such as broader than 500 nm. In one embodiment the spectral width is restricted to wavelength in the visible, i.e. such that a spectral width of more than 200 nm, preferably as a spectral width of more than 200 nm between 400 and 800 nm. In the context of the present text the spectral width is defined as the wavelength region where the output spectral power density is at least about 1 μW/nm.

As briefly mentioned, the light source of the present invention comprises advantageously a non-linear crystal optimized for sum frequency mixing. To achieve frequency conversion in such non-linear crystal requires that two beams are impinging on it. The frequency conversion will depend on phase matching between the two incoming beams and the frequency converted beam. An advantage of this approach is that the second beam can have a larger intensity than the SC beam and hence increase the efficiency of the frequency conversion. Preferable this second beam is extracted from the SC source, at a position prior to the non-linear fiber and sent through a delay unit providing a variable delay stage so that it arrives at the non-linear crystal simultaneously with the output from the SC source. Furthermore the two beams might be recombined prior to the non-linear crystal, see FIG. 15. Thus in one embodiment the non-linear crystal is optimized for sum frequency mixing between the output from the SC source and a second output extracted from the SC source prior to that the beam has traversed the non-linear filter. In one embodiment the second output from the SC source is amplified and/or sent through a variable delay stage and/or frequency doubled prior to reaching the non-linear crystal.

The addressable market for the light source increases if it is possible to extend the tunable output range from the UV and into the visible or even near-IR range. However, as the output of SC sources span these wavelengths this has found to be relatively easily achieved as will explained in the following.

In one embodiment of the invention, the output of the SC source is split before the light impinges on the non-linear crystal. A part of the light is sent through the non-linear crystal to achieve a tunable output pulse in the UV, as prior described. In one embodiment the remaining part of the light is sent through a tunable wavelength filter, which is adjustable to change the spectral output after the filter. Examples of such filters are acousto optical tunable filters (AOTF) or a combination of position dependent optical filters (such as e.g. Linear Variable Filters from the Danish company Delta). Such filters are commonly used for filtering existing SC sources, e.g. in the SuperK Varia and SuperK Select products from NKT Photonics, Denmark. In one embodiment the splitting is done in a polarization splitting element or a wavelength flattened coupler or splitter. An example of such a broadly tunable light source is shown in FIG. 16. Optionally the two outputs (162, 6) can be recombined to the same beam path and/or a shutter can be included on either one of or both of the beams.

The invention also comprises an illumination source for time resolved measurements comprising a tunable optical light source as claimed and as described herein.

Advantageously the illumination source is configured for use in time resolved fluorescence and/or time correlation single photon counting.

In one embodiment the illumination source is configured for use in photoluminescence, DNA sequencing, single photon counting, single molecule detection, intrinsic fluorescence, time resolved photoluminescence, UV polymerisation of resin, DNA sequencing, confocal microscope, FLIM, FRET, flow cytometry, cell-sorting, spectroscopy and/or food analysis.

The invention also comprises an optical measurement system for time resolved measurements comprising a tunable optical light source as claimed and as described herein in combination with a streak camera, which is an instrument for measuring the variation in a pulse of light's intensity with time.

DETAILED DESCRIPTION OF THE INVENTION

FIG. 14 shows the pulse duration of a tunable pulsed source as measured with a streak camera.

FIG. 15 shows a light source according to the invention, where the non-linear crystal 3 is optimized for sum frequency mixing.

FIG. 16 shows a very broad band light source according to the invention where the output extends into the visible range.

The figures are schematic and may be simplified for clarity. Throughout, the same reference numerals are used for identical or corresponding parts.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
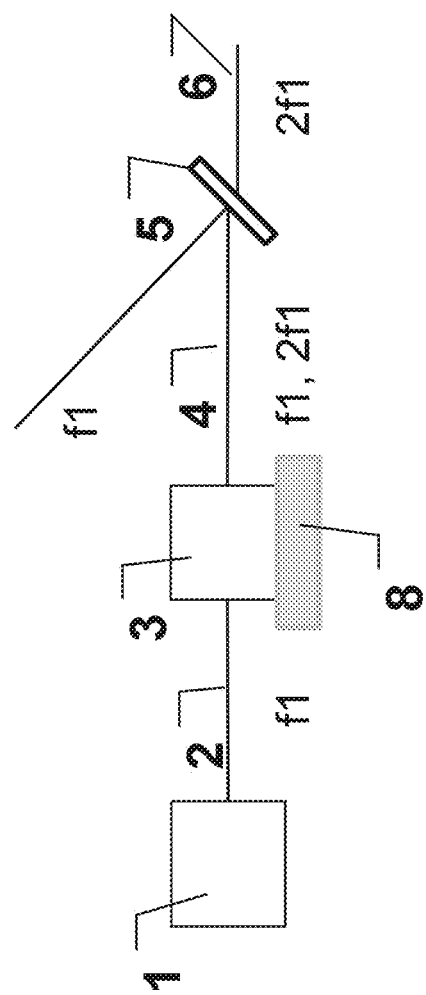
FIG. 1 shows a schematic frequency doubling unit from prior art.

FIG. 1 shows a schematic frequency doubling unit from prior art. It consists of a laser light source 1 emitting light photons at a frequency of f1 2, a non-linear crystal 3 converting some of the light photons to the doubled frequency 2f1 and a wavelength filter 5 for separating the light at f1 and 2f1. To optimize the frequency doubling the non-linear crystal is mounted in a holder 8 which allows changing the position, orientation and/or temperature of the crystal.

Figure 2:
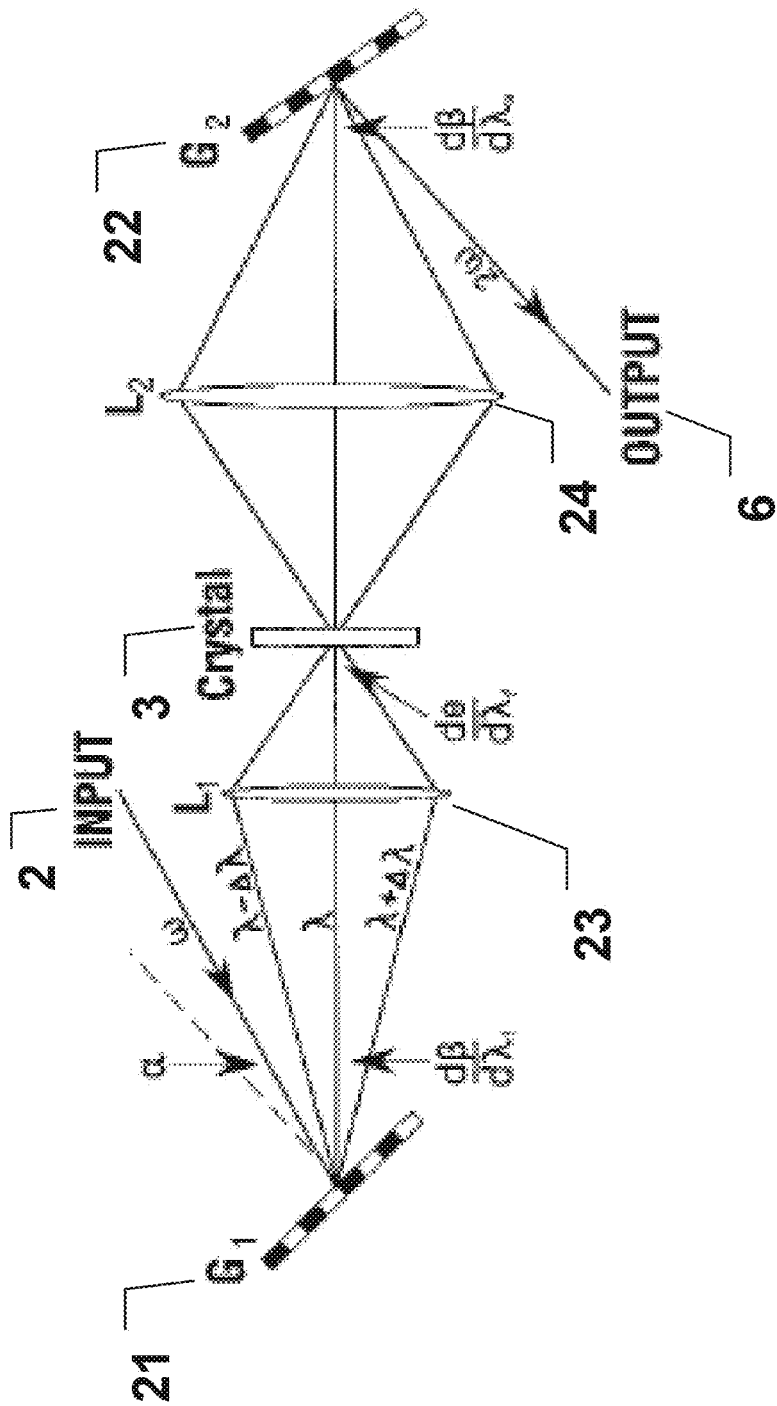
FIG. 2 shows a prior art demonstration of a broadband frequency doubler for broadband pulses, as published by Szabo.

FIG. 2 shows a prior art demonstration of a broadband frequency doubler, as published by Szabo. The input light is dispersed on a diffraction grating 21 and subsequently focused by a lens 23 to reach high intensity on the non-linear crystal 3. After the non-linear crystal another focusing element 24 and diffraction grating 22 are used to achieve the broadband frequency doubled output 6.

Figure 3:
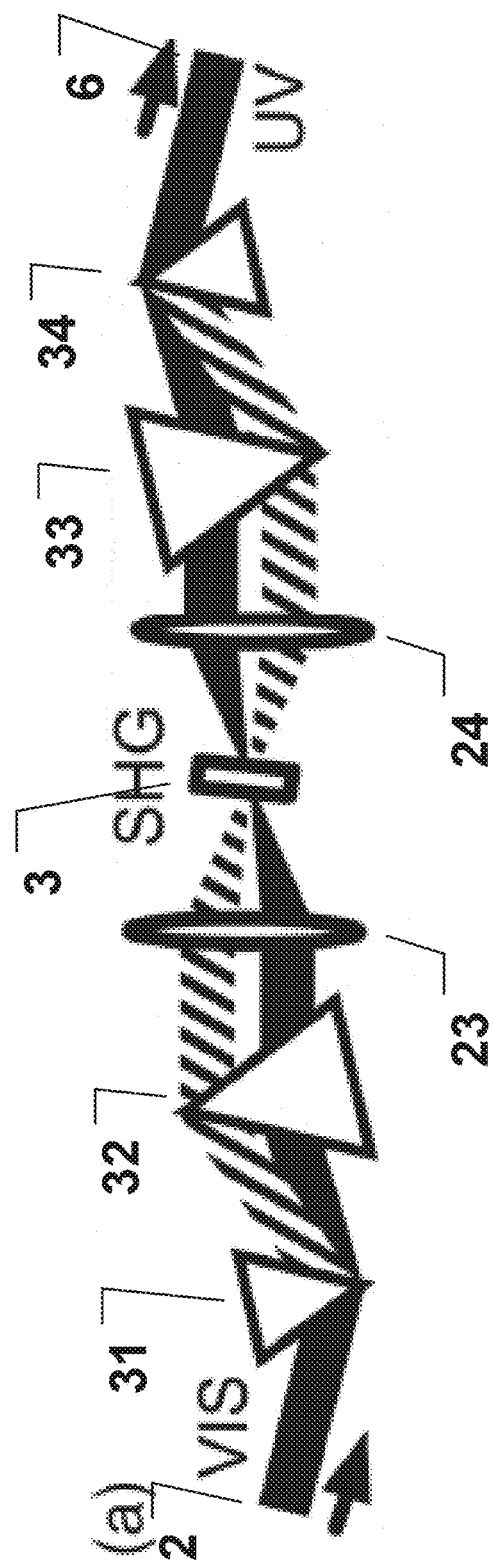
FIG. 3 shows a prior art demonstration of a broadband frequency doubler for broadband pulses, as published by Baum.

FIG. 3 shows a prior art demonstration of a broadband frequency doubler, as published by Baum. The input light is dispersed on a set of prisms 31 and 32 and subsequently focused by a lens 23 to reach high intensity on the non-linear crystal 3. After the non-linear crystal another focusing element and set of prisms 33 and 34 are used to achieve the broadband frequency doubled output 6.

Figure 4:
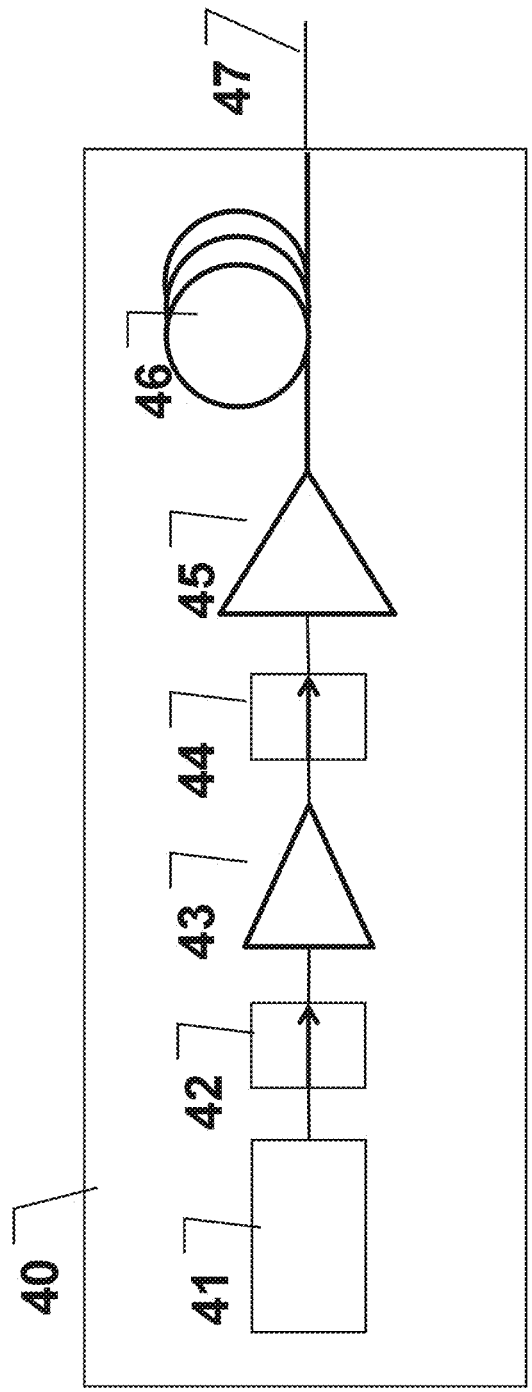
FIG. 4 shows a prior art super continuum source.

FIG. 4 shows a prior art super continuum source 40. Light pulses are generated in a SEED laser 41 and amplified in two sets of amplifiers 43, 45, in between each stage there is an isolator 42, 44. After the last amplifier the light enters a non-linear fiber 46 to generate the super continuum output 47.

Figure 5:
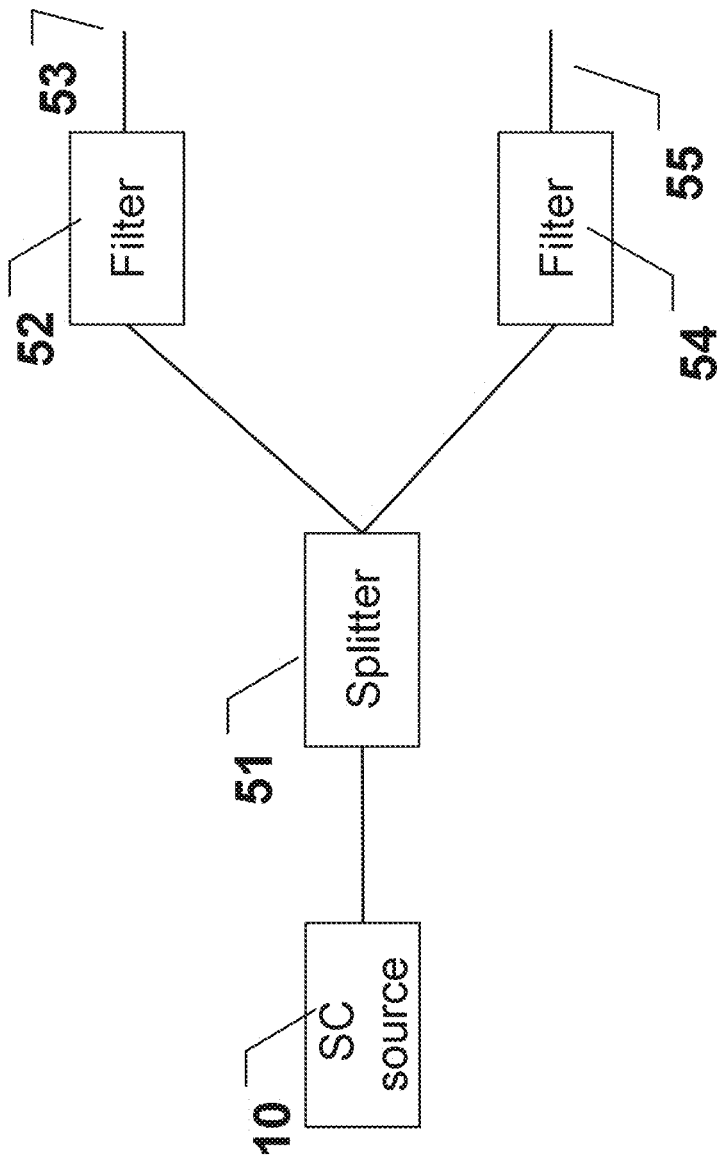
FIG. 5 shows a prior art filtering system for a super continuum source.

FIG. 5 shows a prior art filtering system for a super continuum source. The output from the super continuum light source 47 is sent through a wavelength splitter 51, which divides the output into a low wavelength and a high wavelength part. Each of these spectra is subsequently sent through a tunable filter 52, 54.

Figure 6:
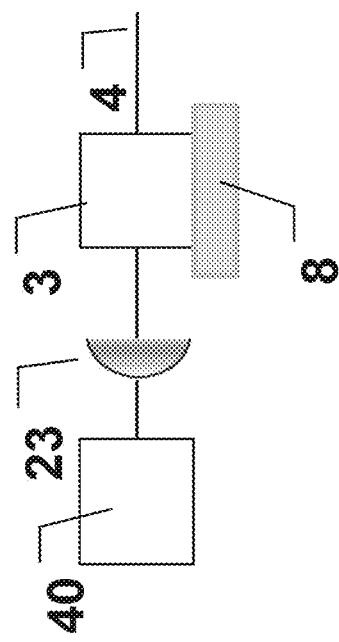
FIG. 6 shows a tunable pulsed source according to the invention.

FIG. 6 shows a tunable pulsed source according to the invention comprising a super continuum light source 40, a focusing element 23, a non-linear crystal 3, and a holder for the non-linear crystal 8. Ref no. 4 indicates the frequency doubled output.

Figure 7:
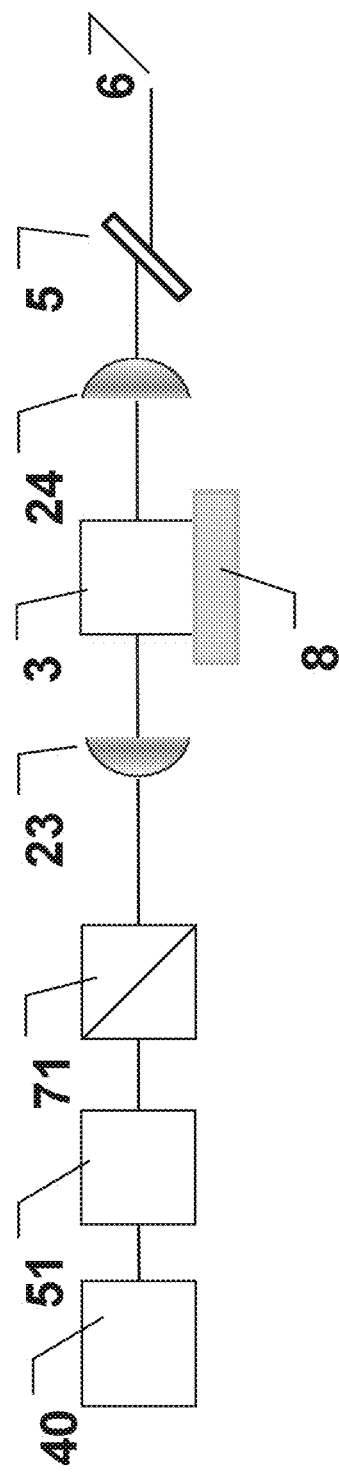
FIG. 7 shows a tunable pulsed source according to the invention. This embodiment is used to generate the experimental data shown in FIGS. 8 to 14.

FIG. 7 shows a tunable pulsed source according to the invention. In addition to the elements shown in FIG. 6 it comprises a wavelength splitter (51), a polarizing element 71 arranged to receive the light prior to entering the non-linear crystal 3, a focusing element 23 and a wavelength filter 5 arranged to receive the light after it has traversed the non-linear crystal. All of these added features are optional for the invention. Ref no. 6 indicates the frequency doubled output.

Figure 8:
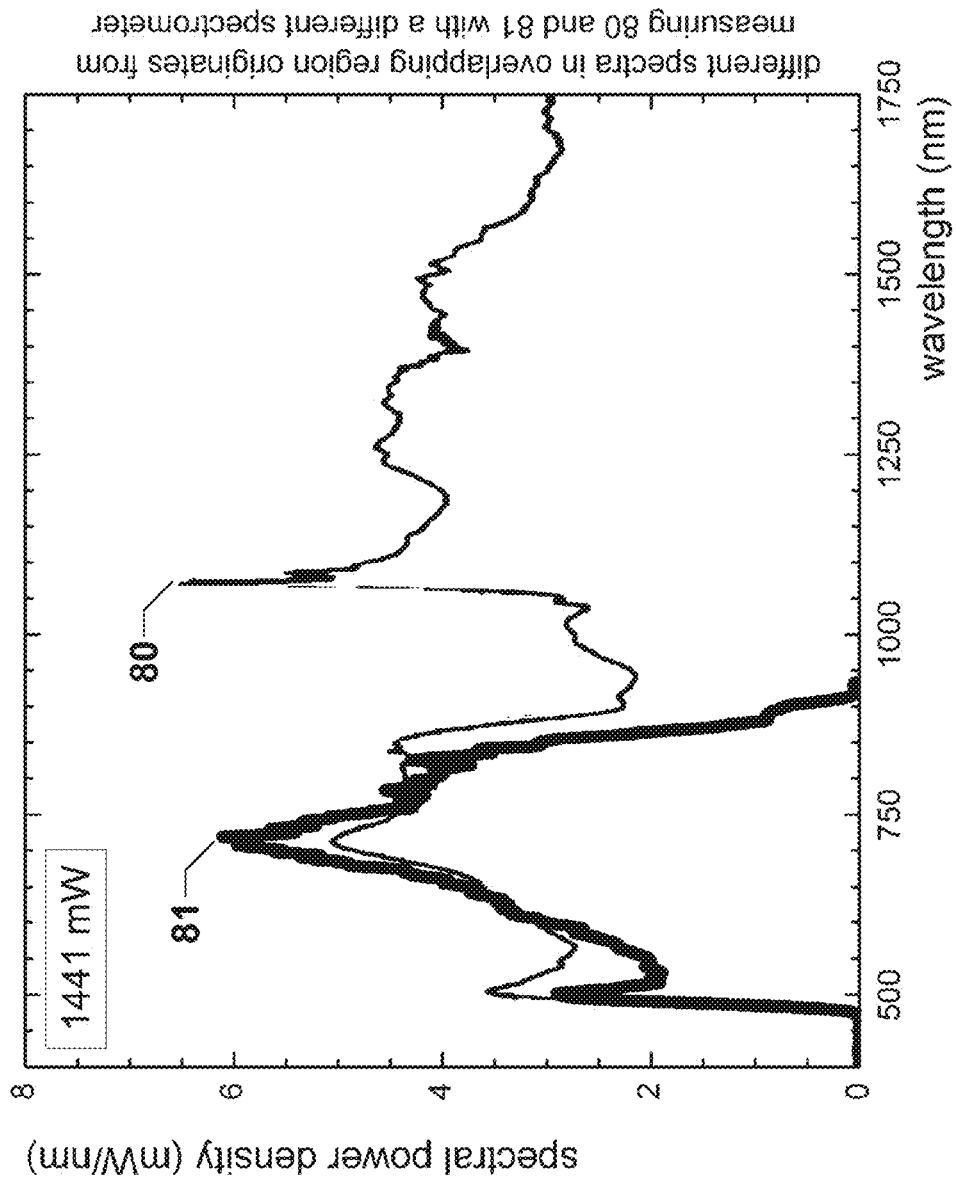
FIG. 8 shows the power spectral density of a SC source 80 and after that the spectrum has been filtered in a low pass filter 81.

The following text describes a number of experiments conducted with a pulsed source, as shown in FIG. 7. The SC source 40 is a SuperK EXR-15 from NKT Photonics. The SEED in the SC source has repetition rate $f_{SEED}$ of 78 MHz, and a pulse length $t_{SEED}$ of approximately 5 ps. The SC source was filtered in a low pass filter 51, which transmits light below approximately 900 nm. After the filter the spectral density of the SC source is more than 1 mW/nm from 500 nm to 900 nm. The power spectral density of the source 80 is shown in FIG. 8, which also shows the power spectral density after the filter 81.

Figure 9:
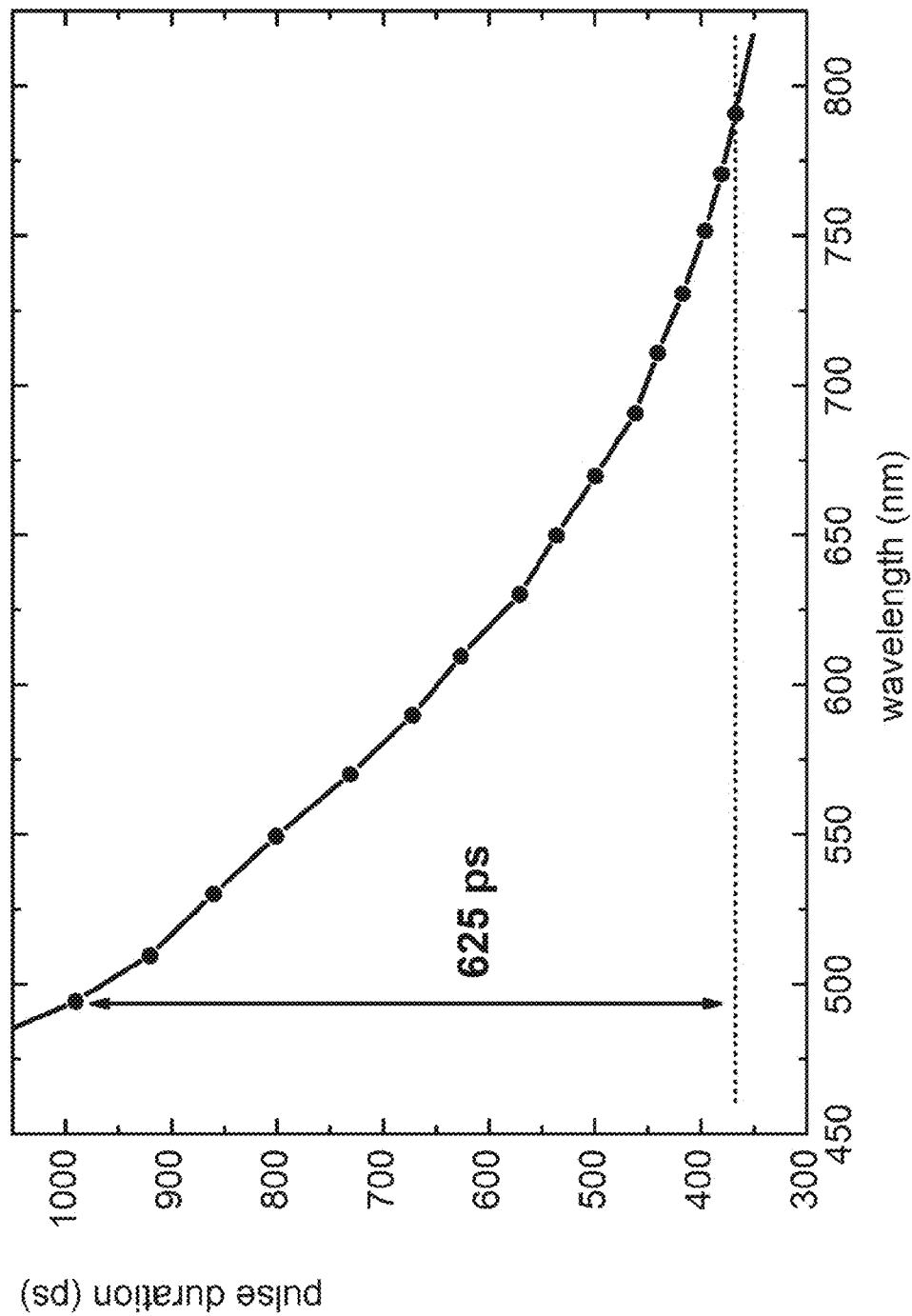
FIG. 9 shows the pulse arrival time as a function of wavelength from a SC source. The difference in arrival time between the light at 500 nm and the light at 800 nm is more than 600 ps.

The pulse arrival time as a function of wavelength from a SC source was measured on a streak camera from Hamamatsu, and is shown on FIG. 9. It is noted that the pulse arrives sooner for larger wavelengths, i.e. smaller arrival time on the figure. The difference in arrival time for light at 500 nm and a 900 nm is more than 600 ps, which is far longer than the pulse duration. Hence this prohibits doubling the entire spectrum simultaneously.

Thus in one embodiment the light source comprises a wavelength dependent time delay arranged to receive the light after the filter and before the non-linear crystal. In one embodiment the wavelength dependent filter has a delay which decreases with wavelength.

After the filter, the light was sent through a polarizing element 71 which was a set of Glan-Taylor α-BBO prisms from Laser Components. The focusing element 23 is an achromatic lens with a focal length of 25 mm from Thorlabs. The non-linear crystal 3 is a Type I cut BBO from Laser Components. Crystal lengths of 2 and 4 mm, and crystal cut angle of 32 degree and 45 degree were tested. The best crystal depends on the application as will be detailed later.

The collimating element 24 was a Fused silica lens with a focal length of 50 mm from Thorlabs. It was observed that a 30 mm lens also worked well for the application. It is noted that care should be taken when specifying the coating, e.g. the standard UV coating from Thorlabs ranges from 290 to 370 nm.

The subsequent wavelength filter 5 is intended to remove non-UV light. If not possible to get the desired contracts with a single filter then multiple filters can be used, examples include Schott UG5 (250 nm-330 nm), Schott BG3 (300 nm-350 nm) and Schott BG18 (350 nm-600 nm). Here the wavelengths in brackets denote the region where the filter has large transmission.

A collection of output spectra were taken with a NA of the focusing lens of 0.06 and using a 4 mm Type I cut BBO crystal having a crystal angle of 32 degree. The NA was varied by letting the beam propagate different distances prior to reaching the focusing lens. It could also be varied by using a telescope prior to the lens.

Figure 10:
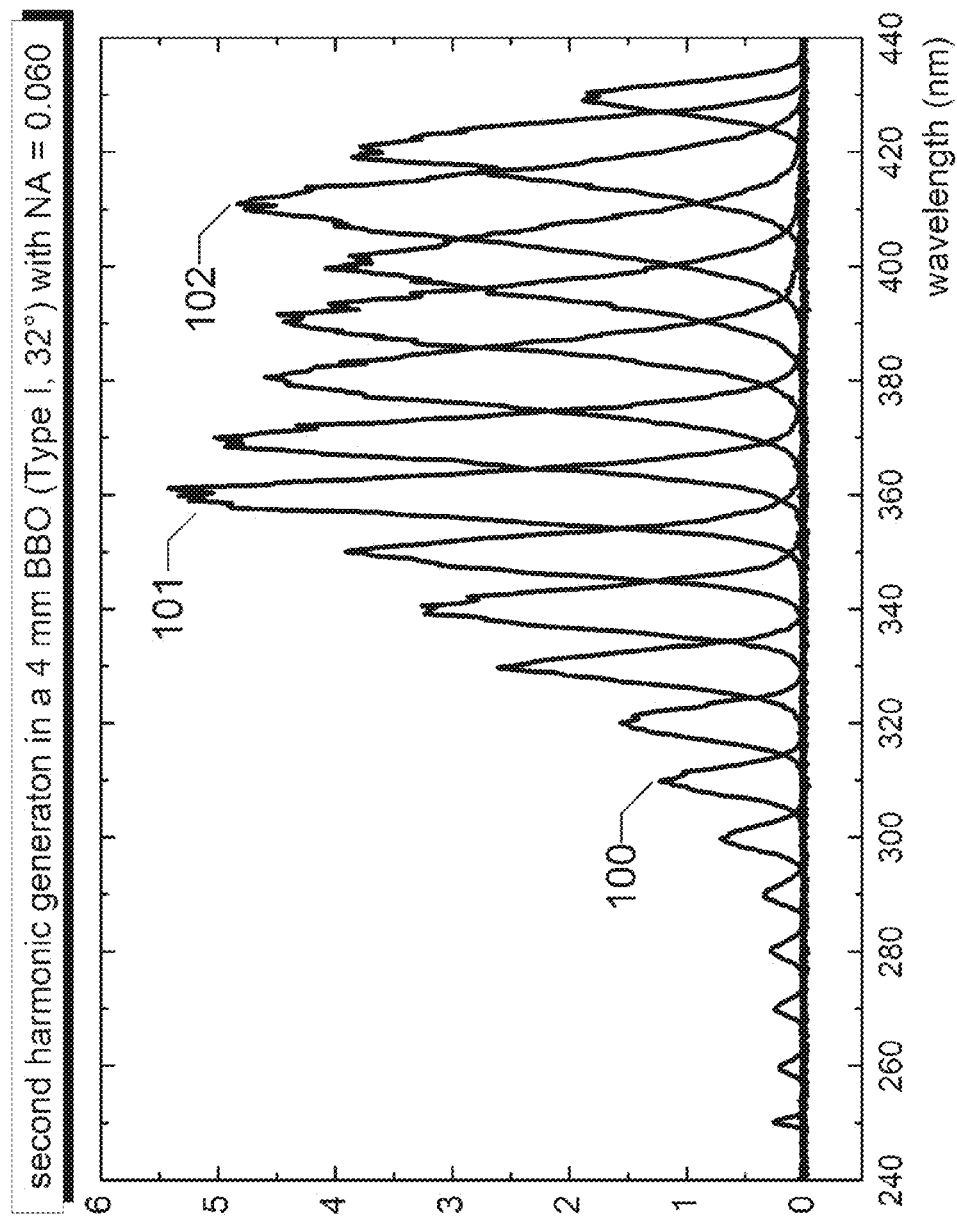
FIG. 10 shows a collection of output spectra from a tunable pulsed source according to the invention.

FIG. 10 shows a collection of output spectra from the tunable pulsed source according to the invention. One example is the spectra 100 containing wavelengths from roughly 305 nm to 315 nm with a central output wavelength $w_{fc}$ of 310 nm. Other examples 101, 102 have central output wavelengths of around 360 nm and 410 nm.

It is observed that the spectral power density decreases for wavelengths below 300 nm. This is due to that the SuperK EXR-15 power density decreases below 600 nm and due to the low acceptance bandwidth and angle of the BBO crystal. Thus the power density in the low wavelength region could be increased by using a SC source with more power below 600 nm, such as e.g. SuperK EXW-12 from NKT Photonics and/or by using a crystal with a larger acceptance bandwidth.

The inventors have performed a number of calculations showing that to frequency double the spectral region between 700 to 900 nm a 4 mm thick BBO Type I cut at 32° is preferred. However, to double the spectral region from 500 and 700 nm a 4 mm thick BBO Type I cut at 45° would be the best.

Figure 11:
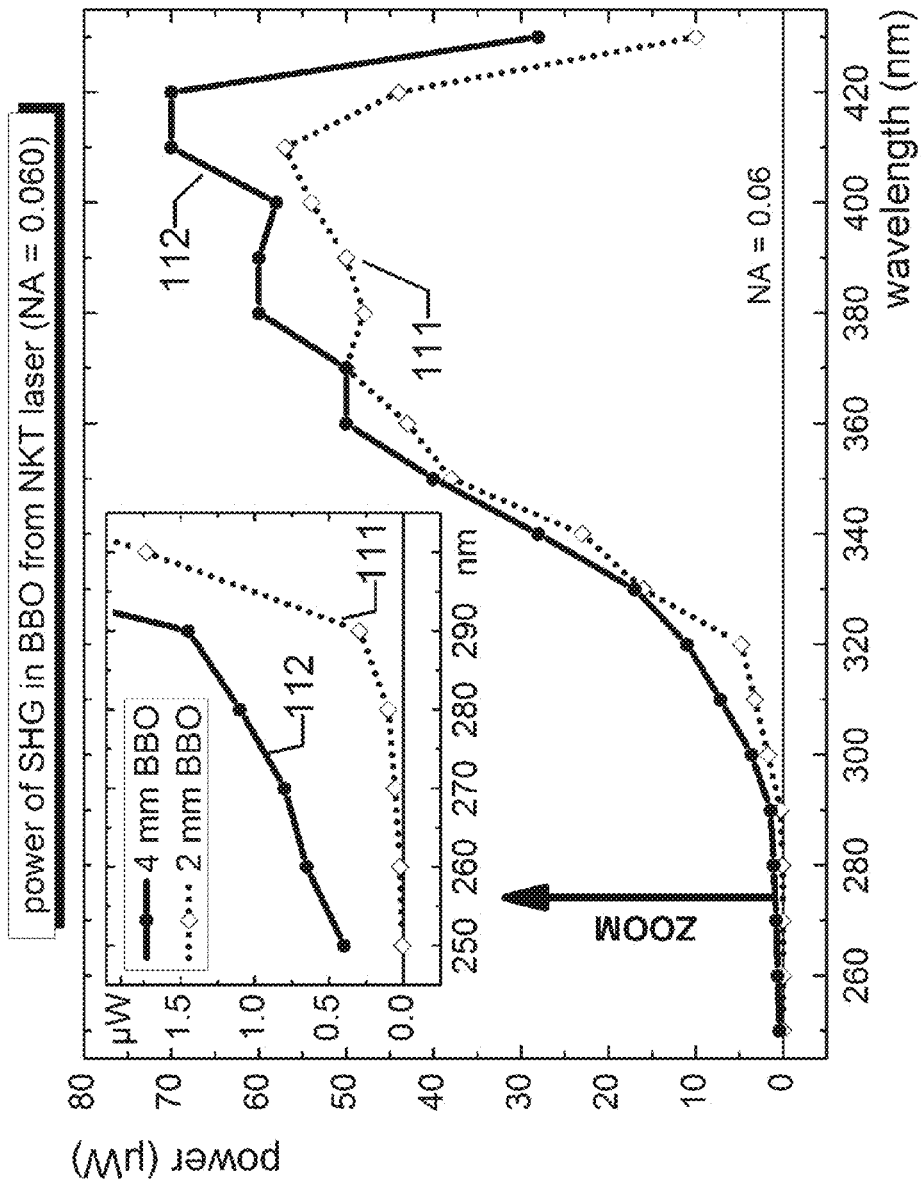
FIG. 11 shows the spectral power output from a tunable pulsed source according to the invention for a crystal length of 2 mm 111 and 4 mm 112.

FIG. 11 shows the spectral power output from a tunable pulsed source according to the invention for a crystal length of 2 mm 111 and 4 mm 112. The power at each wavelength is measured when the pulsed source is optimized for high output power at this particular wavelength.

Figure 12:
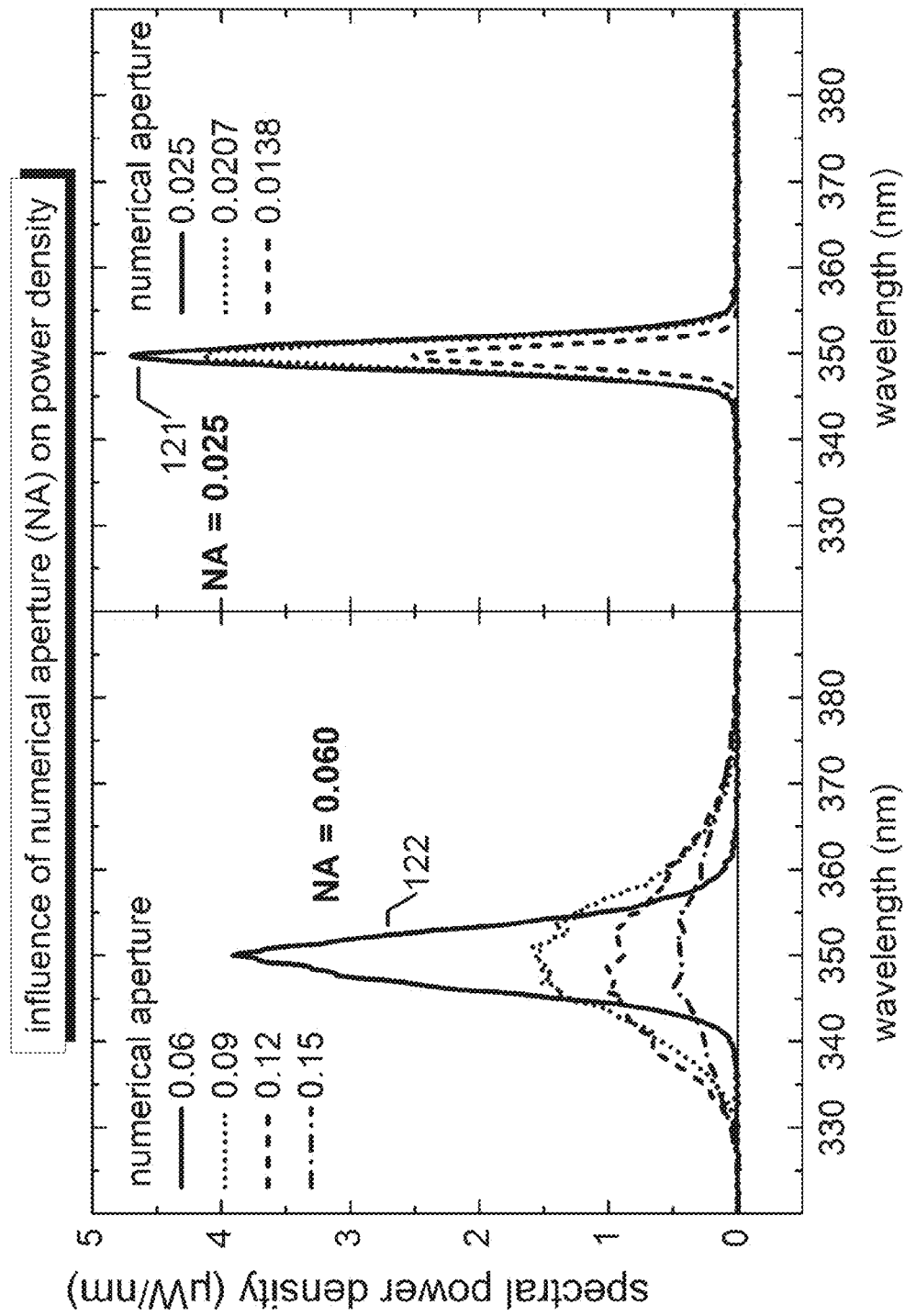
FIG. 12 shows the spectral output as a function of the NA at a central wavelength of 350 nm.

FIG. 12 shows the spectral power density as a function of the NA for a central wavelength of 350 nm. The peak power 121 has a maximum with an NA of 0.025; a slightly broader spectrum 122 is obtained with an NA of 0.06. In general it is found the NA giving the maximum spectral density will vary with wavelength. Furthermore it is expected that it will be different for different types of crystals.

Figure 13:
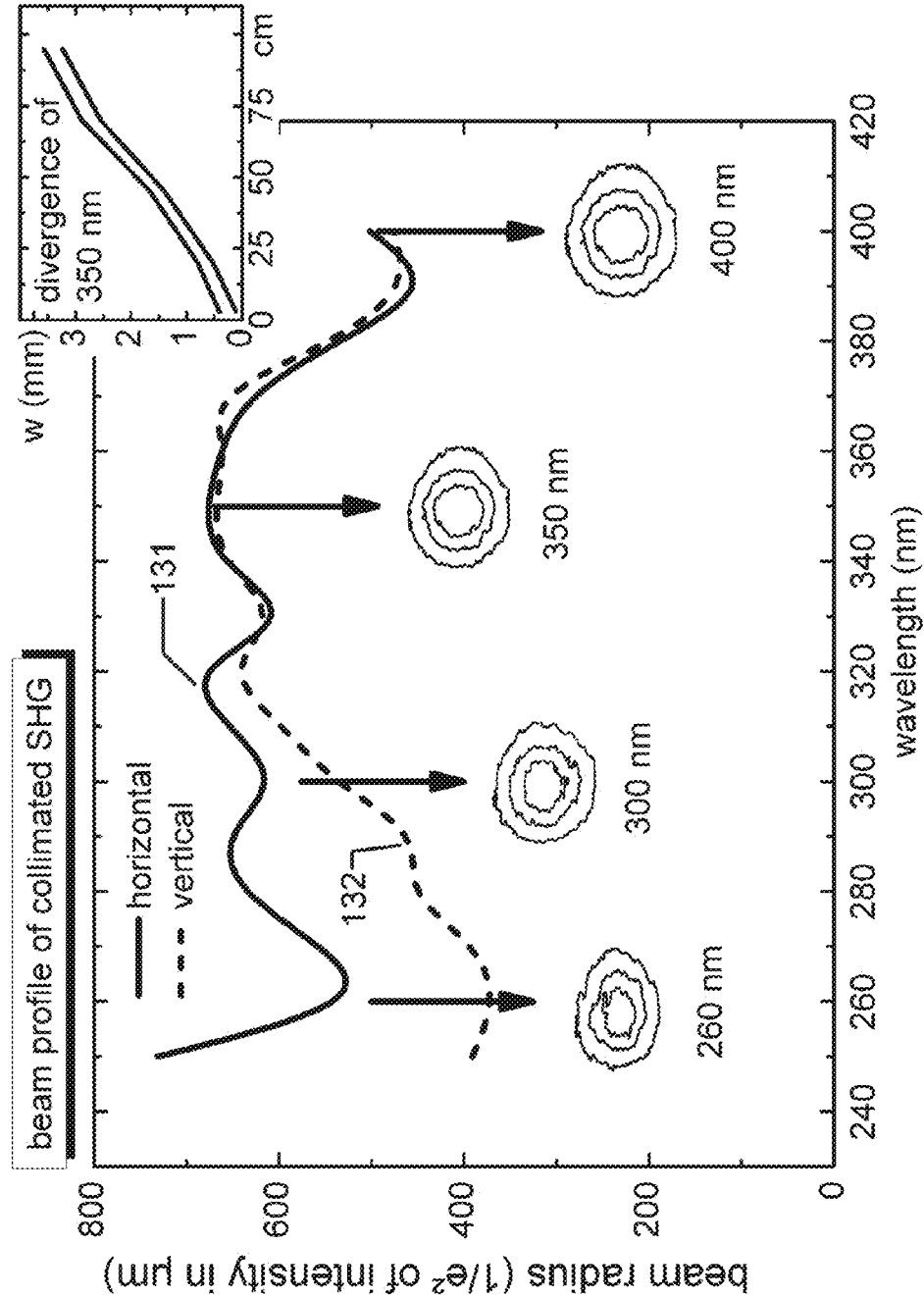
FIG. 13 shows the horizontal 131 and vertical beam radius 132 as a function of wavelength.

As mentioned, the set-up used for these experiments contain a focusing lens 24. FIG. 13 shows the horizontal 131 and vertical beam radius 132 as a function of wavelength.

The pulse length of the UV pulses was measured with a streak camera from Hamamatsu. It was observed that the pulse length decreased with wavelength from 34 ps at 280 nm to 28 ps at 400 nm and 16 ps at 440 nm. FIG. 14 shows the streak camera measurements at 280 nm 141 and at 400 nm 142.

FIG. 15 shows a light source according to the invention, where the non-linear crystal 3 is optimized for sum frequency mixing. In this embodiment a second beam is extracted from the SC source, at a position prior to the non-linear fiber 150, it is redirected on beam manipulating elements 151, 153, and sent through a variable delay stage 152, and recombined with the output from the SC source 154 so that the two beams arrive at the non-linear crystal at the same time as the output from the SC source.

FIG. 16 shows a very broad band light source according to the invention. It comprises two outputs. The first output origins from the non-linear crystal, and is similar to the configuration shown in FIG. 7. The second output is split from the first before the light reaches the non-linear crystal in a polarization splitter 71. Subsequently it is redirected by a beam manipulating element 161 and optionally filtered in a tunable filter 52.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features of the inventions including ranges and preferred ranges can be combined in various ways within the scope of the invention, unless there are specific reasons for not to combine such features.

The invention claimed is:

1. A tunable optical light source comprising:
an input light source;
a focusing element;
a non-linear crystal arranged to convert the frequency of at least part of the output spectrum of said input light source; and
a holding unit for said non-linear crystal;
wherein said input light source is a super continuum light source with a spectral bandwidth of at least about 300 nm, said focusing element is arranged for focusing a beam of light from said super continuum light source onto said non-linear crystal and said holding unit is adjustable for changing the frequency converted output wavelength of said non-linear crystal $w_{fc}$ to provide that the lowest obtainable output wavelength $w_{UV}$ of said tunable light source is ultraviolet and wherein said tunable optical light source further comprises a wavelength filter arranged to filter the light before it reaches said non-linear crystal.

2. The turnable optical light source of claim 1 where the output wavelength $W_{UV}$ is about 380 nm or less.

3. The turnable optical light source of claim 1, where said focusing element is integrated in said super continuum light source.

4. The turnable optical light source of claim 1, where said focusing element comprises at least one lens and/or mirror.

5. The turnable optical light source of claim 1, where said focusing element is or comprises an achromat.

6. The turnable optical light source of claim 1, where the output beam from said focusing element has a numerical aperture of at least about 0.001.

7. The turnable optical light source of claim 1, where the output beam from said focusing element has a numerical aperture of about 0.25 or less.

8. The turnable optical light source of claim 1, furthermore comprising means for adjusting the NA of the output beam from said focusing element.

9. The light source of claim 1, where the focal length of said focusing element is at least about 9 mm.

10. The turnable optical light source of claim 1, furthermore comprising a polarizing element arranged between the super continuum light source and said non-linear crystal.

11. The turnable optical light source of claim 10 wherein said polarizing element is a Glan-Taylor polarizing prism, a broad band polarization splitter cube, a polarizer and/or a wire grid.

12. The turnable optical light source of claim 1, where said non-linear crystal is selected from lithium triborate ($LiB_3O_5$=LBO), cesium lithium borate ($CsLiB_6O_{10}$ CLBO), β-barium borate (β-$BaB_2O_4$=BBO), bismuth triborate ($BiB_3O_6$=BIBO), cesium borate ($CSB_3O_5$=CBO), Yttrium calcium oxyborate (YCOB), strontium beryllium borate ($Sr_2Be_2B_2O_7$=SBBO) or potassium aluminum borate ($K_2Al_2B_2O_7$).

13. The turnable optical light source of claim 12 wherein said non-linear crystal is a Type I cut BBO crystal.

14. The turnable optical light source of claim 12, wherein said non-linear crystal has a length which is at least about 0.5 mm.

15. The turnable optical light source of claim 1, wherein said holding unit is adjustable for positioning said non-linear crystal in the focus position of the light from said focusing element.

16. The turnable optical light source of claim 15 where said holding unit is arranged to adjust the phase-matching angle and thereby said output wavelength $w_{fc}$ without changing the distance to said focusing element.

17. The turnable optical light source of claim 1, further comprising a collimating element arranged to receive the light after it has traversed said non-linear crystal.

18. The turnable optical light source of claim 1, wherein said wavelength filter is an optical glass filter, a low pass filter, a pass band filter and/or a dicroic mirror.

19. The turnable optical light source of claim 1, wherein the spectrum of the light at the input of said non-linear crystal has a spectral bandwidth of at least about 100 nm.

20. The turnable optical light source of claim 1, wherein the output of said super continuum light source is polarized.

21. The turnable optical light source of claim 1, wherein the input super continuum light source comprises a pulsed master oscillator, one or more amplifiers, and a nonlinear fiber which transforms input pulses into a broad band super continuum, and wherein the pulse length after the last amplifier ($t_{MOPA}$) is about 100 ps or less.

22. The turnable optical light source of claim 1, wherein the super continuum light source comprises a pulsed master oscillator, one or more amplifiers, and a nonlinear fiber which transforms input pulses into a broad band super continuum, and wherein the pulse length after the last amplifier ($t_{MOPA}$) is at least about 500 fs.

23. The turnable optical light source of claim 1, wherein the pulse length of the super continuum light source ($t_{SC}$) is about 100 ps or less.

24. The turnable optical light source of claim 1, wherein the pulse length of the super continuum light source ($t_{SC}$) is at least about 500 fs.

25. The turnable optical light source of claim 1, wherein the super continuum light source comprises a non-linear fiber with a length of about 10 m or less.

26. The turnable optical light source of claim 1, wherein the super continuum light source is fiber based.

27. The turnable optical light source of claim 1, wherein the super continuum light source comprises a SEED laswer wherein the SEED laser has a wavelength between 1000 and 1100 nm.

28. The turnable optical light source of claim 1, wherein the output wavelength $w_{fc}$ is computer controlled.

29. The turnable optical light source of claim 1, wherein the super continuum light source comprises a non-linear fiber with a longitudinal axis, the fiber is tapered along at least a length section along its longitudinal axis.

30. The turnable optical light source of claim 1, further comprising a wavelength dependent time delay unit arranged to receive the light after having traversed said wavelength filter and before reaching said non-linear crystal.

31. A tunable optical light source comprising
an input light source;
a focusing element;
a non-linear crystal arranged to convert the frequency of at least part of the output spectrum of said input light source; and
a holding unit for said non-linear crystal;
wherein said input light source is a super continuum light source with a spectral bandwidth of at least about 100 nm and a pulse length $t_{sc}$ of at least about 300 fs, said focusing element is arranged for focusing a beam of light from said super continuum light source onto said non-linear crystal and said holding unit is adjustable for changing the frequency converted output wavelength of said non-linear crystal $w_{fc}$ to provide that the lowest obtainable output wavelength $w_{UV}$ of said tunable light source is ultraviolet and wherein said tunable optical light source further comprising a wavelength filter arranged to filter the light before it reaches said non-linear crystal.

32. The turnable optical light source of claim 31 and where the output wavelength $w_{UV}$ is about 380 nm or less.

33. An illumination source for time resolved measurements comprising a tunable optical light source as claimed in claim 31.

34. An illumination source according to claim 33 configured for use in time resolved fluorescence and/or time correlation single photon counting.

35. An illumination source according to claim 33 wherein the pulse length $t_{UV}$ of said illumination source is about 100 ps or less.

36. An illumination source according to claim 33 wherein the pulse length $t_{UV}$ of said illumination source is at least about 500 fs.

37. An illumination source according to claim 33 configured for use in photoluminescence, DNA sequencing, single photon counting, single molecule detection, intrinsic fluorescence, time resolved photoluminescence, UV polymerisation of resin, DNA sequencing, confocal microscope, FLIM, FRET, flow cytometry, cell-sorting, spectroscopy and/or food analysis.

38. An optical measurement system for time resolved measurements comprising a tunable optical light source as claimed in claim 31 and a streak camera.

39. The tunable optical light source of claim 1, wherein said holding unit is adjustable to move the non-linear crystal with respect to the incoming beam of light from the focusing element, such that it impinges on a new spot.

40. The tunable optical light source of claim 31, wherein said holding unit is adjustable to position the non-linear crystal in the focus position of the beam of light from the focusing element.

41. The tunable optical light source of claim 31, wherein said holding unit is adjustable to move the non-linear crystal with respect to the incoming beam of light from the focusing element, such that it impinges on a new spot.

42. The turnable optical light source of claim 1, wherein the frequency converted output wavelength of said non-linear crystal $w_{fc}$ comprises UV pulses with a duration of at least 27.5 ps.

43. The turnable optical light source of claim 1, wherein said supercontinuum light source comprises pulses with a duration of at least 350 ps.

44. A tunable optical light source comprising:
an input light source;
a focusing element;
a non-linear crystal arranged to convert the frequency of at least part of the output spectrum of said input light source; and
a holding unit for said non-linear crystal; and
a computer;
wherein said input light source is a super continuum light source with a spectral bandwidth of at least about 300 nm, said focusing element is arranged for focusing a beam of light from said super continuum light onto said non-linear crystal and said holding unit is adjustable for changing the frequency converted output wavelength of said non-linear crystal $w_{fc}$ to provide that the lowest obtainable output wavelength $w_{UV}$ of said tunable light source is ultraviolet, wherein adjustment of the holding unit is computer controlled, said computer being programmed to receive feedback from the output light and to adjust the holding unit to a desired position.

* * * * *